(12) United States Patent
McAuliffe et al.

(10) Patent No.: US 7,871,987 B2
(45) Date of Patent: Jan. 18, 2011

(54) ESTER DERIVATIVES OF ASCORBIC AND 2-KETO ACID SACCHARIDES

(75) Inventors: Joseph C. McAuliffe, Sunnyvale, CA (US); Wyatt Charles Smith, Tiburon, CA (US); Michael S. Starch, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 885 days.

(21) Appl. No.: 11/792,460

(22) PCT Filed: Dec. 16, 2005

(86) PCT No.: PCT/US2005/045991
§ 371 (c)(1), (2), (4) Date: Jun. 6, 2007

(87) PCT Pub. No.: WO2006/066227
PCT Pub. Date: Jun. 22, 2006

(65) Prior Publication Data
US 2008/0118454 A1    May 22, 2008

Related U.S. Application Data

(60) Provisional application No. 60/636,567, filed on Dec. 16, 2004.

(51) Int. Cl.
| | | |
|---|---|---|
| A61K 31/7012 | (2006.01) | |
| A61K 31/7024 | (2006.01) | |
| A61K 31/695 | (2006.01) | |
| A61K 31/25 | (2006.01) | |
| A61K 31/215 | (2006.01) | |
| A61K 31/22 | (2006.01) | |
| A61K 31/23 | (2006.01) | |
| C07H 13/02 | (2006.01) | |
| C07H 13/04 | (2006.01) | |
| C07F 7/04 | (2006.01) | |
| C07F 7/08 | (2006.01) | |
| C07F 7/18 | (2006.01) | |

(52) U.S. Cl. .......................... 514/54; 514/63; 514/530; 514/548; 514/551; 514/552; 514/546; 536/55; 536/55.3; 536/119; 556/437; 556/430; 556/457; 556/489; 556/482

(58) Field of Classification Search ...................... None
See application file for complete search history.

(56) References Cited

PUBLICATIONS

Wagner et al., "Silicon-Modified Carbohydrate Surfactants III: Cationic and Anionic Compounds" Applied Organometallic Chemistry (1997) vol. 11, pp. 523-538.*

Akimoto et al., "Preparation of oligodimethylsiloxanes with sugar moiety at a terminal group as a transdermal penetration enhancer" Macromolecular Chemistry and Physics (2000) vol. 201, pp. 2729-2734.*

* cited by examiner

*Primary Examiner*—Eric S Olson
(74) *Attorney, Agent, or Firm*—Dinsmore & Shohl LLP

(57) ABSTRACT

Novel ester derivatives of ascorbic acid and 2-keto-acid saccharides are provided wherein the ester is introduced by ester bond formation between at least one hydroxy-functionality on the ascorbic acid or 2-keto-acid saccharide and a carboxy-functional organosiloxane, or between a 2-keto-gulonic acid and a hydroxy-functional organosiloxane, as well as methods for their synthesis. Treatment, cosmetic, and personal care formulations comprising the novel esters are also provided, including controlled release forms thereof.

50 Claims, 4 Drawing Sheets

Potential Ascorbic acid generation by transesterification of 2-KLG silicone

2-KLG ester-functional siloxane

Intramolecular lactonization results in the generation of free ascorbic acid

Ascorbic acid carbinol-functional silicone

ESTER DERIVATIVES OF ASCORBIC AND 2-KETO ACID SACCHARIDES

CROSS-REFERENCE TO RELATED APPLICATIONS

This application is a national stage application of PCT/US05/45991, filed Dec. 16, 2005, which claims benefit of provisional application 60/636,567, filed Dec. 16, 2004.

The present invention relates to compounds comprising ester derivatives of ascorbic acid and 2-keto acid saccharides, including stereoisomers thereof, processes for their manufacture, and methods of use. The ester function includes organosiloxanes comprising at least one carboxy functional end group or hydroxy functional end group, or a combination thereof. The organosiloxanes are covalently bound to the sugar via formation of an ester bond. The resultant sugar-functional siloxane compounds are miscible in various silicone-based substances, retain the anti-oxidant and other beneficial properties of the sugar moiety, demonstrate desirable surfactant properties, and have desirable utility in treatment, cosmetic and personal care applications.

Ascorbic acid is a reducing sugar consisting of a cyclic lactone of a saccharide acid. L-Ascorbic acid and D-erythorbic acid (a diastereoisomer of ascorbic acid, also known as isoascorbic acid) are well-known agents with utility in the food safety, pharmacological and cosmetic arts. For example, keto acid sugars are therapeutically effective for topical treatment of various cosmetic conditions and dermatologic disorders including dry skin, acne, dandruff, keratoses, age spots, wrinkles and disturbed keratinization and, in particular, ascorbic acid and related compounds are of known utility in skin-lightening and other technologies related to hyperpigmentation. Ascorbic acid, as well as other sugar formulations, however, are prone to oxidation and are easily destabilized. In addition cosmetic or pharmacological compositions comprising these acids may damage tissue or irritate human skin on repeated topical applications due to lower pH of the formulations.

Ester derivatives of ascorbic acid are known and have been used for decades in applications that exploit them as fat-soluble materials having anti-oxidant properties. Ascorbyl palmitate (structure 2) and ascorbyl oleate (structure 3) are representative of this class of compounds with commercial applications in food oil preservation, bread crumb softening, fruit juice browning inhibition and personal care. Recently, ascorbic acid esters have also been studied for their potential anti-cancer properties. However, these compounds exhibit poor miscibility with silicone based materials and, in particular applications, do not confer the benefits of a silicone-based vehicle. Additionally, these compounds exhibit low levels of skin and other keratinaceous tissue permeability and penetration when compared to silicone-based materials.

Hence, ascorbic acid and other keto acids have been traditionally compounded with other hydrophobic materials to improve their stability and performance. For example, combinations of ascorbic acid and silicone are well-known. U.S. Pat. No. 6,146,664 to Mukhtar discloses formulations comprising particulate ascorbic acid suspended in a polyorganosiloxane vehicle and useful in topical applications to reduce wrinkles and increase collagen growth and elasticity. In these formulations, the ascorbic acid is not solublized in the silicone vehicle. The preferred silicone oil is an organosiloxane and gel and solid forms are preferred while emulsifying forms are excluded. U.S. Pat. No. 5,750,123 to Znaiden et al. discloses cosmetic compositions comprising ascorbic acid stabilized by dimethyl isosorbide in a pharmaceutically acceptable carrier. Znaiden teaches that aesthetic properties are improved by the presence of a crosslinked non-emulsifying siloxane elastomer and a volatile siloxane.

Various commercial products directed to skin care are also available which comprise ascorbic acid and silicone polymer in compounded mixtures. For example, 840 Citrix Antioxidant Serum, marketed by Clavin Labs, comprises, inter alia, cyclomethicone, L-Ascorbic Acid, Silicone Polymer, Dimethicone, and Dimethicone Copolyol. Stableact® system products, comprise ascorbic acid in silicone emulsions. In Stableact® C Plus, for example, hydrophilic actives, ascorbic acid and green tea are contained in a propylene glycol phase that is then dispersed in a silicone base.

WO 0130784 to Herve et al. discloses ether-linked ascorbic acid-siloxane compounds and details the synthesis of several exemplary compounds from protected ascorbic acid derivatives and organosilanes. Akimoto, T., Kawahara, K., and Nagase, Y., *Macromol. Chem. Phys.* 2000, 201, 2729-2734 teach glucopyranosyl-terminated oligodimethylsiloxanes covalently coupled via ether or thioether linkages. Brandstadt et al., U.S. Patent Application Serial Nos. US200400820224, US20040077816, disclose the enzyme-catalyzed synthesis of organosiloxane esters and amides wherein the enzyme catalyzes the formation of an ester bond between carboxylic acid, ester or amide functional groups of an organosiloxane and any organic reactant comprising hydroxy functionality.

In addition, in order to avoid the continual need for reapplication and multiple treatments involving potentially irritating agents, slow-release forms of ascorbic acid and other saccharide acids are desirable. 2-Keto-L-gulonic acid, is a known precursor of ascorbic acid which may, under proper bioenvironmental conditions, convert to L-Ascorbic acid. Means of delivering 2-keto-L-gulonic acid to tissues in a form that is amenable to such intra-tissue conversion is not currently known in the art.

Organosiloxanes covalently bound to ascorbic acid or 2-keto acid saccharides via ester bonds are not specifically known in the art. Hence, there is a clear need in the art for compounds comprising ascorbic and ketoacid saccharides covalently bound to organosiloxanes, and, further, there is an established need for improved delivery systems for cosmetic and personal care formulations comprising ascorbic and ketoacid sugars with increased stability and efficacy, and which provide for safer application and treatment protocols.

Accordingly, one embodiment of the present invention is directed to a compound comprising an ester derivative of ascorbic acid or a 2-keto acid saccharide, wherein an ester has been introduced by an ester bond formation between an ascorbic acid or a 2-keto acid saccharide comprising at least one hydroxy-functional group and a carboxy-functional organosiloxane, wherein the ascorbic acid comprises either ascorbic acid or isoascorbic acid, as well as stereoisomers or salts thereof, and wherein the 2-keto acid saccharide comprises either 2-keto-L-gulonic acid or 2-keto-D-gluconic acid or esters, including stereoisomers or salts thereof. The ester bond may be formed between any carboxy functionality of the organosiloxane and any free hydroxyl located at any position on the ascorbic acid or 2-keto acid saccharide.

Another embodiment is directed to compounds comprising an ester derivative of a 2-keto acid saccharide wherein an ester function has been introduced by ester bond formation between a 2-keto acid saccharide and a hydroxy-functional organosiloxane, wherein 2-keto-acid saccharide comprises either 2-keto-L-gulonic acid or 2-keto-D-gluconic acid or salts thereof.

The present invention also provides process embodiments for the manufacture of the novel compounds. One such embodiment is directed to a method for synthesizing the ester derivatives of ascorbic acid or 2-keto acid saccharides. The method comprises: a) providing a protected ascorbic acid or a protected 2-keto acid saccharide by forming a protecting group from at least one hydroxy-functional group; b) mixing the protected ascorbic acid or protected 2-keto acid saccharide with a carboxy-functional organosiloxane to form a solution; c) contacting the solution with a biocatalyst which is capable of catalyzing ester bond formation under conditions that promote ester bond formation; d) optionally, removing the protecting group. It is contemplated that the protecting group may comprise a functional group with desirable functionality beyond its role in blocking reactivity of the hydroxy group. In some embodiments the functional groups remain bound to the saccharide after the esterification reaction with the organosiloxane.

Another process of manufacture embodiment provides a method for synthesizing ester derivatives of 2-keto acid saccharides through the carboxylic acid functionality of the saccharide. The method comprises: a) providing a protected 2-keto acid saccharide by forming a protecting group from at least one of the hydroxy-functional groups; b) providing a hydroxy-functional organosiloxane; c) dissolving the protected 2-keto-acid saccharide and the hydroxy-functional organosiloxane in a suitable solvent to form a solution; d) treating the solution with a biocatalyst which is capable of catalyzing ester bond formation under conditions that promote ester bond formation; e) optionally, removing the protecting group, and wherein the protecting group may comprise a functional group. In specific embodiments the 2-ketoacid saccharide comprises 2-keto-L-gulonic acid or 2-keto-D-gluconic acid.

The present invention also provides embodiments directed to treatment, cosmetic, and personal care compositions. In one embodiment the treatment, cosmetic or personal care composition comprises an ester derivative of ascorbic acid. In controlled-release embodiments the treatment, cosmetic or personal care formulation comprises an ester derivative of an ascorbic acid precursor, specifically 2-keto-L-gulonic acid. Under certain conditions the ester derivative of 2-keto-L-gulonic acid undergoes intramolecular lactonization and free ascorbic acid is generated. In one embodiment the treatment, cosmetic or personal care formulation comprises a keratinaceous tissue lightening comprising the inventive ester derivates of ascorbic acid or its precursor. In a very specific embodiment the treatment formulation treats conditions and disorders associated with hyperpigmentation.

Figure 1:
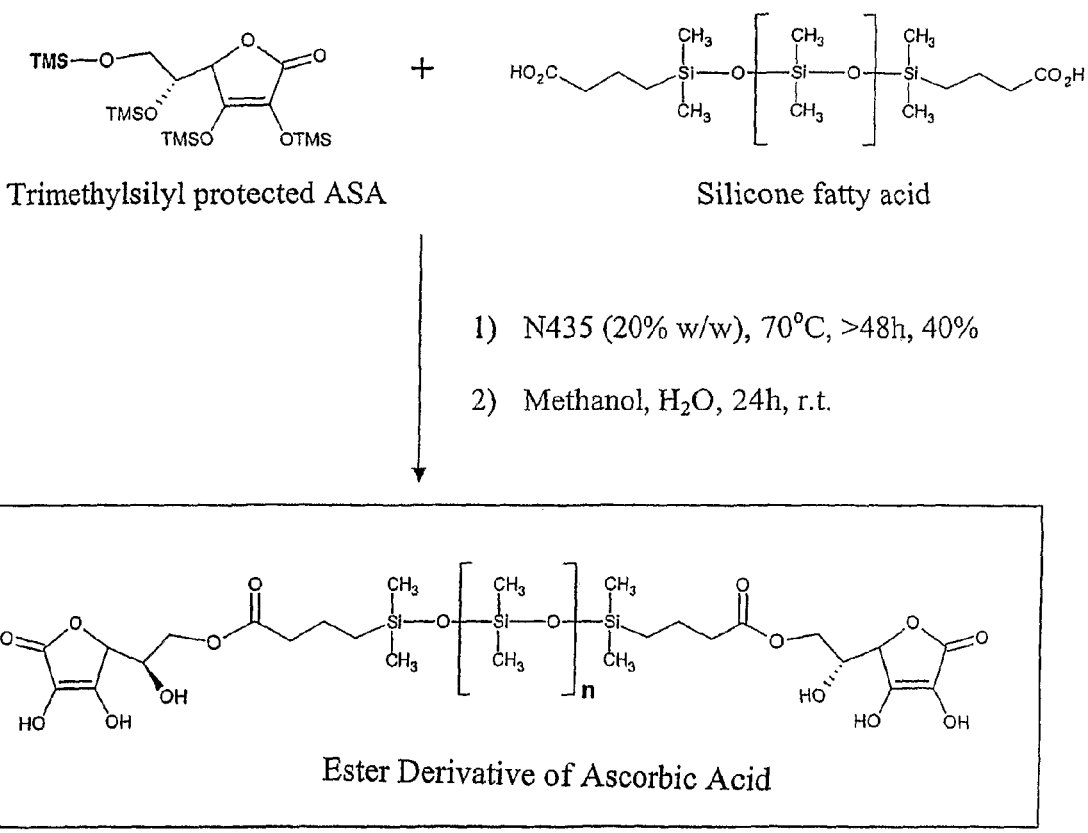
FIG. 1 illustrates the synthesis of an ester derivative of ascorbic acid wherein an ester bond is formed between a trimethylsilyl-protected ascorbic acid and a bis-carboxy functional siloxane.
Figure 2:
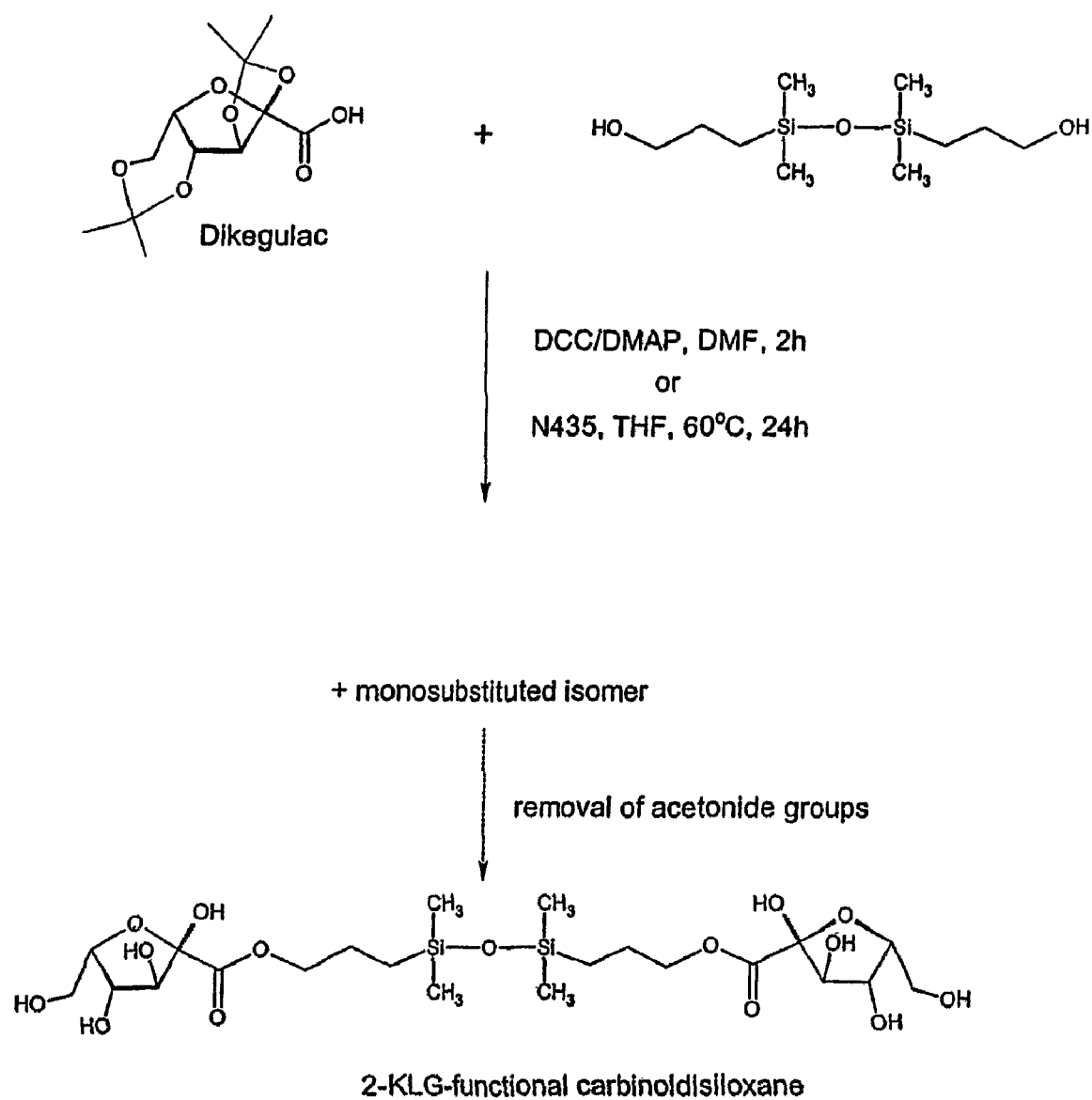
FIG. 2 illustrates the synthesis of an ester derivative of 2-keto L-gulonic acid from di-kegulac and a bis-carbonyl functional siloxane.
Figure 3:
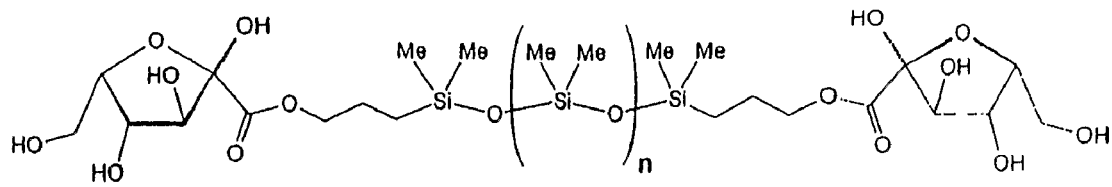
FIG. 3 illustrates a scheme for generating ascorbic acid from an ester derivative of 2-keto-L-gulonic acid via intramolecular lactonization.
Figure 3:
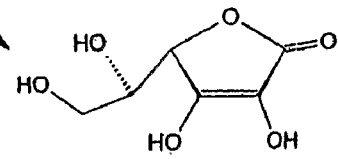
Figure 3:
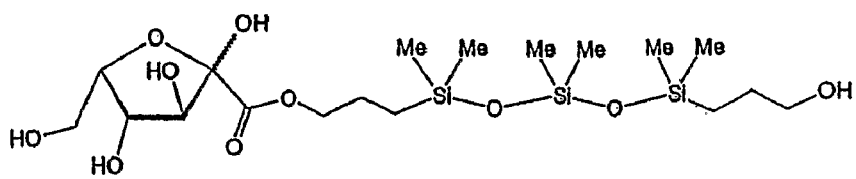
Figure 3:
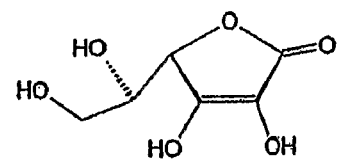
Figure 3:

The present invention provides novel compounds comprising ester derivatives of ascorbic acid, isoascorbic acid and 2-keto acid saccharides. The novel ester derivatives of ascorbic acid are formed from an esterification reaction between a hydroxy-functional ascorbic acid and a carboxy functional organosiloxane. The esterification reaction is catalyzed by a biocatalyst. Such biocatalysis provides an enhanced capability of regional- and stereo-specificity with respect to the reaction products. The ester derivatives of the 2-keto-acid saccharide are formed from either an esterification reaction between a 2-keto-acid saccharide comprising at least one free hydroxyl and a carboxy-functional organosiloxane, or between the carboxylic acid group of a 2-keto acid saccharide and a hydroxy-functional (carbinol) organosiloxane. It is apparent to one of ordinary skill in the art that the scope of the inventive compounds includes all ester derivatives of ascorbic acid, isoascorbic acid, and 2-keto-acid saccharides wherein the organosiloxane is covalently bound to the ascorbic, isoascorbic or 2-keto-acid-saccharide acid via an ester bond.

As used herein the term "ascorbic acid" includes ascorbic acid and its diastereoisomer, isoascorbic acid unless specifically referred to as L-ascorbic acid or D-erythorbic acid, and salts thereof. The fourth and fifth carbon atoms of an ascorbic acid molecule are chiral, leading to the existence of two enantiomeric isomers at each chiral center for a total of 4 diasteroisomers. One of the enantiomers of Isoascorbic acid is also known as D-erythorbic acid. Due to its strong reducing properties, D-erythorbic acid has similar technological applications to L-ascorbic acid as a water-soluble antioxidant. "Ascorbic acid" also includes the derivatives of all diastereoisomers, including those wherein one or more of the free hydroxy functional groups thereof are formed as esters, ethers, ketones, and so forth, and including those comprising groups intended to be protecting and/or functional groups.

As used herein the term "2-keto acid saccharide" includes 2-keto L-gulonic acid and its stereoisomer, 2-keto D-gluconic acid, unless otherwise specified, and salts thereof. "2-keto acid saccharide" also includes the derivatives of both stereoisomers, including those wherein one or more of the free hydroxy functional groups thereof are formed as esters, ethers, ketones, and so forth, and including those comprising groups intended to be protecting and/or functional groups.

Accordingly, one embodiment of the present invention is directed to a compound comprising an ester derivative of ascorbic acid or 2-keto acid saccharide, wherein an ester function has been introduced by an ester bond formation between an ascorbic acid comprising at least one hydroxy-functional group or a 2-keto acid saccharide comprising at least one hydroxy-functional group, and a carboxy-functional organosiloxane, wherein the ascorbic acid comprises either ascorbic acid or isoascorbic acid, or their stereoisomers or salts thereof, and wherein the 2-keto acid saccharide comprises 2-keto L-gulonic acid or 2-keto D-gluconic acid or esters or their stereoisomers or salts thereof. In one embodiment, the organosiloxanes comprise polydialkylsiloxanes comprising carboxy-functionality at one or both termini linked to the organosiloxane through a linker moiety. In other embodiments, the polydialkylsiloxanes comprise pendant carboxy functionality or a combination of terminal and pendant carboxy functionality. In a specific embodiment the organosiloxanes comprise polydimethylsiloxanes. In another specific embodiment the organosiloxane comprises a mono or bis-carboxyalkyl-functional organosiloxane. In one very specific embodiment, the ester derivative comprises a 6-O acyl derivative of either an ascorbic acid or a 2-keto acid saccharide, though the inventive ester derivatives should not be construed as limited to those formed from esterification at this location.

As used herein the term "protecting group" includes groups formed involving one or more of the free hydroxy functional groups of the ascorbic acid or saccharide, and includes esters, ethers, ketones and so forth. In one embodiment, the process to form the ester derivative comprises "protecting" at least one of the hydroxyl groups of the ascorbic acid or derivatives thereof as esters (for example, as acetate esters) or ethers (for example, methyl ethers or), epoxys, or cyclic ketals. In a specific embodiment the ascorbic acid is protected at one or more hydroxyl sites by initial conversion to the cyclic ketal by the formation of 2,3-isopropylidene-ascorbic acid. Also as used herein the term "protecting" group may include a functional group, or added functionality may not relate to "protecting" at all. In one embodiment, the ascorbic acid comprises at least one hydroxy group which is functionalized or protected or both.

In another specific embodiment, the ascorbic acid is protected at one or more hydroxyl sites as esters (for example as O-carbonates, O-acetates, O-phosphates and the like). The latter may then be derivatized using biocatalyzed esterification methods described below ultimately to produce the structures of the present invention. In addition, the formation of mono and diphosphates of ascorbic acid are described thoroughly in the literature. For example, U.S. Pat. No. 4,939,128 to Kato et al., the contents of which are incorporated herein by reference, teaches the formation of phosphoric acid esters of ascorbic acid. Similarly, U.S. Pat. No. 4,999,437 to Dobler et al., the contents of which are also fully incorporated herein by reference, describes the preparation of ascorbic acid 2-phosphate. In another specific embodiment the ascorbic acid is protected at the hydroxyls by formation of ethers, and in a very specific embodiment the protecting moiety is a trimethylsilyl ether. Any of these known ascorbic acid derivatives can be used within the scope of the present invention.

One may also produce the ascorbic acid functional organosiloxanes according to the present invention via hydrosilylation reactions. For instance, by employing 10-undecylenic acid or ester derivatives thereof, in place of a carboxydecyl-functional siloxane, a 6-O-ascorbyl undecylenate may be generated, which may then be optionally converted to one its hydroxyl-protected forms such as that bearing trimethylsilyl ether groups. The ascorbyl undecylenate may then be coupled to a hydrido-functional organosiloxane though contact with a hydrosilyation catalyst such as those derived from platinum to yield an ascorbic acid functional organosiloxane according to the present invention.

In very specific embodiments TMS ether protective groups may be used to permit chemical esterification between, for example, methyl 2-keto-L-gulonic acid and bis-carboxypropyl-functional polydimethylsiloxane. Methyl 3,4,5-tri-O-trimethylsilyl-2-keto-L-gulonic acid, which may be generated from methyl 2-keto-L-gulonic acid from a combination of hexamethyldisilazane (HMDZ) and acetonitrile according to methods known in the art, may be treated with bis-carboxypropyl-functional polydimethylsiloxane in the presence of an ester bond-forming reagent such as dicyclohexylcarbodiimide (DCC) and a base, to yield a 6-O-acylated methyl 2-KLG derivative. Removal of the remaining TMS ether protective groups and any residual solvent yields the methyl 2-KLG ester derivative of carboxypropyl-functional polydimethylsiloxane.

In another specific embodiment, sulfuric acid may be used to promote the esterification of ascorbic acid and carboxy-functional disiloxanes. In this embodiment, the point of esterification is not limited to the primary hydroxyl of the ascorbic acid moiety. For example 1,3-bis-(10-carboxydecyl)-1,1,3,3-tetramethyldisiloxane is treated with ascorbic acid using sulfuric acid as both solvent and catalyst at room temperature for several hours resulting in the esterification of the carboxylic acid groups with ascorbyl moieties.

One embodiment of the novel compounds comprising ester derivatives of ascorbic acid may be depicted by the following structural formula:

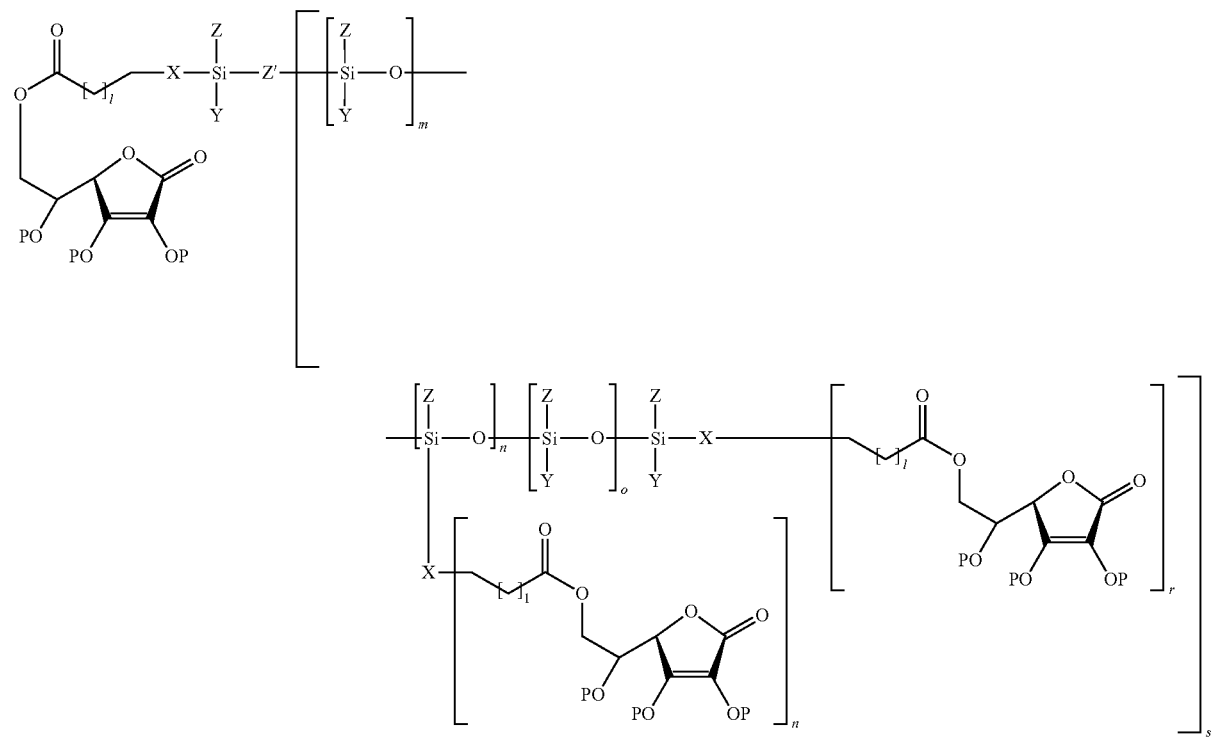

As depicted structurally above: each P is independently be any protecting or functional group, a proton or a cation chosen from the alkali or alkaline earth metals; the fourth and/or fifth carbons of the carbohydrate moieties may be in the alternative enantiomeric positions; s is either 0 or 1; m, n, and o may independently represent any integer between 0 and 300; and l is any integer between 0 and 30; r is either 0 or 1. X may be $CH_2$, $CH_3$, $OCH_2\text{-}[CH_2]_l CH_2$, $OCH_2CH(CH_3)CH_2$, $(OCH_2CH_2)_m OCH_2\text{-}[CH_2]_l CH_2$, $(OCH(CH_3)CH_2)_m OCH_2[CH_2]_l CH_2$, $NHCH_2[CH_2]_l CH_2$, $NHCH_2CH_2NHCH_2[CH_2]_l CH_2$, $NHCH_2CH_2NHCH_2CH(CH_3)CH_2$, $(C{=}O)NHCH_2[CH_2]_l CH_2$, $(C{=}O)NHCH_2CH_2NHCH_2[CH_2]_l CH_2$, or $(C{=}O)NHCH_2CH_2NHCH_2CH(CH_3)CH_2$. X can also be Y or Z. Y and Z are independently selected from H, OH, alkyl (C1-12), carboxyalkyl (C1-12), alkenyl (C1-12), $OSi(CH_3)_3$, $[OSi(Y)(Z)]_m OSi(X)(Y)(Z)$, and phenyl. When s=1, Z'=O. When s=0, Z'=Z.

As is readily apparent from inspection of the formula, the number of silicon atoms in a given ascorbyl siloxane molecule may vary and include as few as one (s=0). The number of silicon atoms in a molecule reflects, as is referred to herein, the degree of polymerization of that molecule, and a molecule having a particular "degree of polymerization" may be referred to herein as DP#, where # is the degrees of polymerization. For example, DP2 may represent any molecule according to the present invention comprising two silicon atoms. Therefore, DP2 represents structural embodiments where s=1, but m, n and o are all 0. Further, for example, DP3 represents structural embodiments where s=1, but m, n and o vary to equal 1 (i.e. 001, 100, 010). DP4 represents structural embodiments where s=1, and m, n and o vary to equal 2 (i.e. 200, 020, 002, 110, 011, 101), and so on. Further, according to the present invention, where # is greater than 2, the ascorbyl siloxane sample so designated may actually constitute a mixture of molecules having different chain lengths, wherein the median chain length is greater than 2. For example, DP15 designates a sample of the presently inventive ascorbyl siloxane wherein the Si chain lengths of the molecules comprising the sample average 15.

In one specific embodiment, an ascorbyl siloxane according to the present invention comprises DP1 to about DP300. In a more specific embodiment, the ascorbyl siloxane comprises DP1 to about DP100. In an even more specific embodiment, the ascorbyl siloxane comprises DP2 to DP20. In a very specific embodiment, the ascorbyl siloxane comprises DP15+/−5. In another very specific embodiment, the ascorbyl siloxane comprises DP2.

It will be apparent to one of ordinary skill in the art that the above structural formula also extends to compounds containing free carboxylic acid groups resulting from either incomplete esterification during synthesis, or as a result of chemical and/or enzymatic hydrolysis of the ascorbyl ester groups. Such free carboxylic acid groups may also be present as their lower alkyl (C1-6) esters.

Another embodiment of the novel compounds comprises ester derivatives of 2-keto acid saccharides formed from an esterification reaction between a carboxy-functional organosiloxane and a free hydroxyl on the 2-keto acid saccharide may be depicted by the following structural formula:

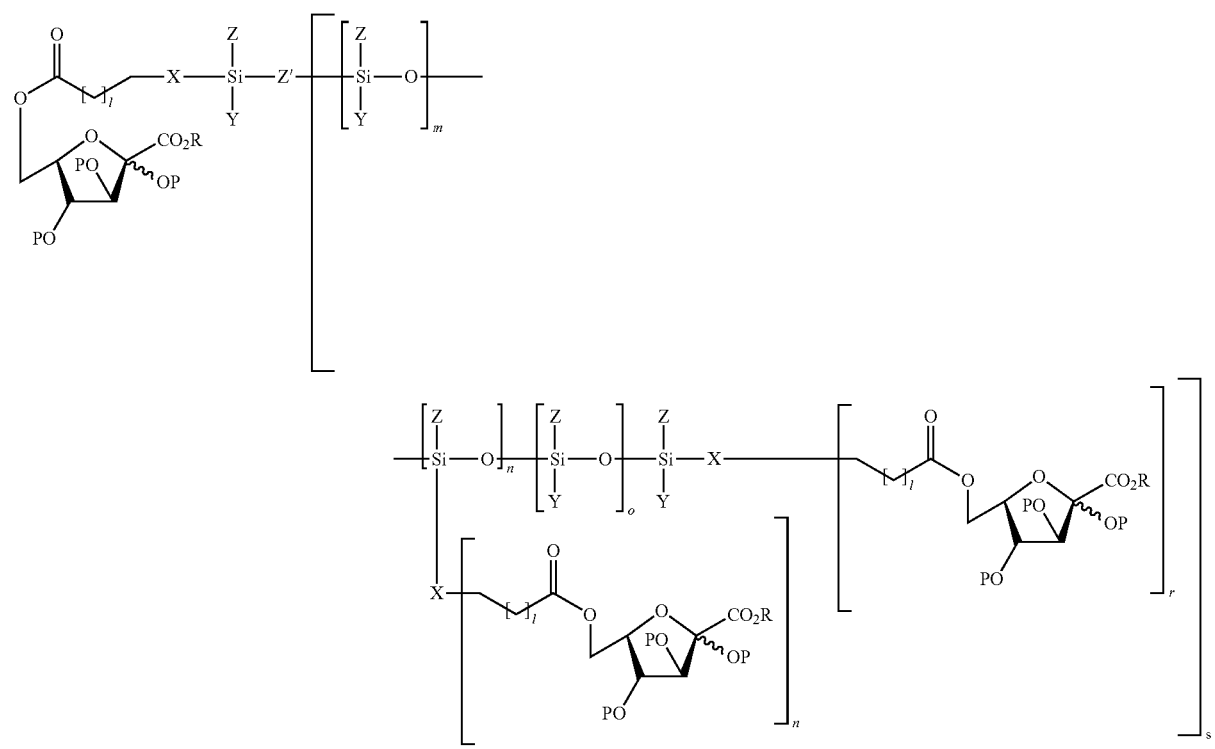

As depicted structurally above: each P may independently be any protecting or functional group or a proton; R can be a lower alkyl (C1-6) or alkenyl (C1-6), a metal ion, $NH_4^+$ or $NH_a(R)_{4-a}$ where R is lower alkyl (C1-6) and a is an integer from 0 to 4, the configurations of either or both of the fourth and fifth carbons of the carbohydrate moieties may be in the alternative enantiomeric positions; s is either 0 or 1; m, n and o may be independently represented by any integer between 0 and 300; and 1 may be any integer between 1 and 30; r is either 0 or 1. X may be $CH_2$, $CH_3$, $OCH_2[CH_2]_lCH_2$, $OCH_2CH$ One embodiment of the novel compounds comprising ester derivatives of 2-keto saccharide acids may be depicted structurally by the following formula:

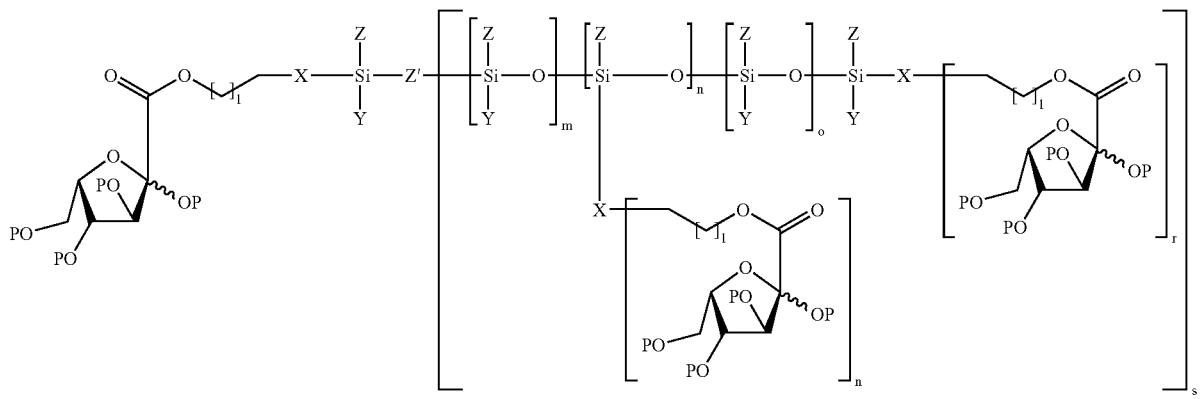

$(CH_3)CH_2$, $(OCH_2CH_2)_mOCH_2[CH_2]_lCH_2$, $(OCH(CH_3)CH_2)_mOCH_2[CH_2]_lCH_2$, $NHCH_2[CH_2]_lCH_2$, $NHCH_2CH_2NHCH_2[CH_2]_lCH_2$, $NHCH_2CH_2NHCH_2CH(CH_3)CH_2$, $(C=O)NHCH_2[CH_2]_lCH_2$, $(C=O)NHCH_2CH_2NHCH_2[CH_2]_lCH_2$, or $(C=O)NHCH_2CH_2NHCH_2CH(CH_3)CH_2$. X can also be Y or Z. Y and Z are independently selected from H, OH, alkyl (C1-12), carboxyalkyl (C1-12), alkenyl (C1-12), $OSi(CH_3)_3$, $[OSi(Y)(Z)]_mOSi(X)(Y)(Z)$, and phenyl. When s=1, Z'=O. When s=0, Z'=Z.

Another compound embodiment of the invention is directed to ester derivatives of 2-keto acid saccharides wherein an ester has been introduced by an ester bond formation between a 2-keto acid saccharide acid and a hydroxy-functional, or carbinol-functional, organosiloxane, and wherein reference to any particular 2-keto acid saccharide includes within its scope any stereoisomers thereof. In one specific embodiment the 2-keto acid saccharide comprises either the 2-keto-L-(2-KLG) or 2-keto-D-(KDG) diastereoisomeric forms, or salts thereof. In a specific embodiment the carbinol-functional organosiloxane comprises a polydimethylsiloxane with carbinol functionality at one or both terminal ends or present within the polymer chain as a pendant functional group. It will be apparent to one of ordinary skill in the art, however, that hydroxy functionality may be present in other locations. In another specific embodiment organosiloxane comprises a mono or bis-carbinol functional organosiloxane.

In a specific embodiment the 2-keto acid saccharide comprises at least one hydroxy group that is functionalized or protected or both. The protected and/or functionalized embodiments are similar to those described for the ester derivatives of ascorbic acid and include derivatives wherein at least one hydroxy group is protected by formation of an ester, an ether, or an epoxy. In a very specific embodiment at least one hydroxyl is protected in the form of an ester, for example as an O-acetate, an O-carbonate, or an O-phosphate. In one specific embodiment the hydroxyl groups of the 2-keto acid saccharide are protected in the form of bis-acetonide (2,3:4,6-bis-O-(1-methylethylidene)-α-L-xylo-2-hexylofuranosonic acid), also known as dikegulac. In this embodiment the acetonide protecting groups may be removed after the biocatalyzed formation of the ester bond to form the novel compound, or they may be retained in some proportion for certain downstream formulation purposes.

As depicted structurally above, each P independently may be any protecting or functional group or a proton, the configurations of either or both of the fourth or fifth carbons of the carbohydrate moieties may be in the alternative enantiomeric positions; s is either 0 or 1, m, n, and o may be independently represented by any integer between 0 and 300, and 1 may be any integer between 1 and 30; r is either 0 or 1. X can be $CH_2$, $CH_3$, $OCH_2[CH_2]_lCH_2$, $OCH_2CH(CH_3)CH_2$, $(OCH_2CH_2)_mOCH_2[CH_2]_lCH_2$, $(OCH(CH_3)CH_2)_mOCH_2[CH_2]_lCH_2$, $NHCH_2[CH_2]_lCH_2$, $NHCH_2CH_2NHCH_2[CH_2]_lCH_2$, $NHCH_2CH_2NHCH_2CH(CH_3)CH_2$, $(C=O)NHCH_2[CH_2]_lCH_2$, $(C=O)NHCH_2CH_2NHCH_2[CH_2]_lCH_2$, or $(C=O)NHCH_2CH_2NHCH_2CH(CH_3)CH_2$. X can also be Y or Z. Y and Z are independently selected from H, OH, alkyl (C1-12), carboxyalkyl (C1-12), alkenyl (C1-12), $OSi(CH_3)_3$, $[OSi(Y)(Z)]_mOSi(X)(Y)(Z)$, and phenyl. When s=1, Z'=O. When s=0, Z'=Z.

The present invention is also directed to methods for synthesizing the novel compounds. According to one embodiment, the method for synthesizing the novel compounds comprising ester derivatives of ascorbic acid or 2-keto acid saccharides comprise: a) providing a protected ascorbic acid or a protected 2-keto acid saccharide by forming a protecting group from at least one hydroxy-functional group of the ascorbic acid or 2-keto acid saccharide; b) mixing the protected ascorbic acid or protected 2-keto acid saccharide with a carboxy-functional siloxane to form a solution; c) contacting the solution with a biocatalyst which is capable of catalyzing ester bond formation under conditions that favor the formation of ester bonds; and d) optionally, removing the protecting group, and wherein the protecting group may comprise a functional group. This synthetic method may take place under solvent-free conditions. Conditions that favor the formation of ester bonds typically involve the removal or sequestration of water or low molecular weight alcohols thus preventing the hydrolysis of the ester functionalities.

In a specific embodiment the hydroxyls are protected in the form of a trimethylsilyl ether, and in a very specific embodiment the protected ascorbic acid comprises a tetra-O-trimethylsilyl ascorbic acid. Protection as a tetra-O-trimethylsilyl derivative allows enhanced miscibility of the ascorbic acid with the carboxy-functional siloxane. Protection as a tetra-O-trimethylsilyl derivative also allows the removal of the 6-O-TMS ether in situ through the action of the carboxy-functional siloxane, an additive such as a tertiary alcohol or water generated as a result of the esterification reaction. The latter also prevents the accumulation of water during the course of the reaction. Removal of the 6-O-TMS ether allows subsequent esterification of the 6-OH group of the otherwise protected ascorbic acid.

One of ordinary skill in the art will appreciate that additional synthetic methods could be used to produce the aforementioned compounds. For example, the linker group could be attached to either ascorbic acid or a 2-keto acid saccharide through ester bond formation, and subsequently the modified linker may be attached to an organosiloxane polymer comprising an appropriate chemistry. In one specific example, an ascorbic acid-modified linker bearing a terminal olefinic function could be attached to a hydride-functional organosiloxane via hydrosilylation.

As used herein, the term "biocatalyst" includes: 1) natural, semi-synthetic, or metabolically engineered catalytic substances that are isolated from biological sources; and 2) synthetic catalytic molecules that mimic biological pathways.

As used herein, the term "enzyme" includes proteins that are capable of catalyzing chemical changes in other substances. The enzymes can be wild-type enzymes or variant enzymes. Enzymes within the scope of the present invention include, but are not limited to, pullulanases, proteases, cellulases, amylases, isomerases, lipases, oxidases, oxidoreductases, hydrolases, aldolases, ketolases, glycosidases, oxidoreductases, hydrolases, aldolases, ketolases, glycosidases, lyases, ligases, transferases, and ligases.

As used herein, the term "lipolytic enzyme" refers to a polypeptide, protein or enzyme exhibiting a lipid degrading capability such as a capability of degrading a triglyceride or a phospholipid. A lipolytic enzyme may be, for example, a lipase, a phospholipase, an esterase or a cutinase. For the present invention, lipolytic activity may be determined according to any procedure known in the art. See, for example, Gupta et al, Biotechnol. Appl. Biochem. (2003) 37:63-71; Andre, Christophe, et al, U.S. Pat. No. 5,990,069 (International Publication WO 96/18729A1).

As used herein, the term "protein" refers to polymers of large molecular mass composed of one or more polypeptide chains and whose monomers are amino acids joined together by peptide bonds. The terms "protein" and "polypeptide" are sometimes used interchangeably herein. The conventional one-letter or three-letter code for amino acid residues is used herein.

In a specific embodiment the biocatalyst comprises an enzyme, and in a more specific embodiment the biocatalyst comprises a hydrolase enzyme. In very specific embodiments the hydrolase enzyme is selected from the group consisting of a lipase, a protease, a phosphoesterase, an esterase, an amidase, a cutinase, and combinations thereof. In an even more specific embodiment the hydrolase enzyme comprises a lipase, and in a further specific embodiment the lipase comprises an immobilized form of *Candida antarctica* lipase B (CALB) marketed as N435 and available from Novozymes (Denmark).

A further method embodiment is directed to the synthesis of novel compounds comprising ester derivatives of 2-keto acid saccharides. The method comprises: a) providing a protected 2-keto acid saccharide by forming a protecting group from at least one of the hydroxy-functional groups; b) providing a hydroxy-functional organosiloxane; c) dissolving the protected 2-keto acid saccharide and the hydroxy-functional organosiloxane in a suitable solvent to form a solution; d) treating the solution with a biocatalyst which is capable of catalyzing ester bond formation; and e) optionally, removing the protecting group, and wherein the protecting group may comprise a functional group.

In a specific embodiment the 2-keto acid saccharide hydroxyls are protected by forming acetonide groups. In a very specific embodiment the 2-keto acid saccharide comprises 2-keto-L-gulonic acid and the protected 2-keto-L-gulonic acid is in the form of Dikegulac, a keto-acid saccharide wherein the hydroxyls are protected by forming the di-acetonide.

In these embodiments the biocatalyst is defined as above, and in specific embodiments the biocatalyst comprises an enzyme. In more specific embodiments the enzyme comprises a hydrolase enzyme, and in further specific embodiments the hydrolase enzyme may comprise a lipase, a protease, a phosphoesterase, an esterase, an amidase, a cutinase, or combinations thereof. In very specific embodiments the hydrolase enzyme comprises lipase and in an even more specific embodiment the lipase comprises *Candida antarctica* lipase B (CALB) in the form of —N435 immobilized lipase. Lipases are particularly desirable hydrolase enzymes in the synthesis of esters of organic acids.

2-KLG, typically in the form of the methyl ester, is a known immediate precursor to L-ascorbic acid. Several routes of conversion are known in the art. Methyl-2-KLG is not oxidatively sensitive and can readily be converted into L-ascorbic acid by a simple acid or base catalyzed cyclization. Hence, successful delivery of 2-KLG to environments what may be manipulated to cause conversion of the 2-KLG to ascorbic acid is possible. In the novel compounds, the ascorbic acid is in a form covalently bound to an organosiloxane that may enhance absorption through and into environments typically resistant to ascorbic acid. Further, in other embodiments of the present invention, the ascorbic acid may be delivered in the form of its precursor, 2-KLG (2-KDG for isoascorbic acid), through delivery as the ester derivative of 2-KLG and post-delivery transesterification and release as free L-ascorbic acid. This release may occur over time as the rate of release may be influenced by the nature of the environment. In addition, manipulation of the environment may be affected such that the rate of release is controlled, and/or reservoirs of ascorbic acid may be produced.

Accordingly, one embodiment of the invention provides a controlled-release method of generating ascorbic acid. The method comprises: a) providing an ester derivative of 2-keto-L-gulonic acid wherein the ester has been introduced by an ester bond formation between a 2-keto-L-gulonic acid and a hydroxy-functional organosiloxane; b) delivering the ester derivative of 2-keto-L-gulonic acid to an environment wherein an intramolecular lactonization reaction may occur, releasing free ascorbic acid and a carbinol-functional organosiloxane.

In a further embodiment of the invention, an ester derivative of 2-KLG attached to a organosiloxane polymer through one of the saccharide hydroxy groups is converted to ascorbic acid such that the ascorbic acid moiety remains attached to the organosiloxane polymer.

According to another embodiment, a cosmetic formulation is provided comprising: an ester derivative of 2-keto acid saccharide wherein the ester has been introduced by an ester bond formation between a 2-keto acid saccharide and a hydroxy-functional organosiloxane; and a cosmetically suitable vehicle or base. In a more specific 2006/066227 PCT/US2005/045991 embodiment the 2-keto acid saccharide comprises either 2-keto-L-gulonic acid or 2-keto-D-gluconic acid. In an even more specific embodiment, the 2-keto acid saccharide comprises 2-keto-L-gulonic acid.

Formulations containing ascorbic acid-functional polysiloxanes are contemplated for use in skin-lightening products. For example an emulsion of an ascorbic acid-functional polysiloxanes and water containing 0.1 to 50% active ascorbic acid is applied to skin over a period of time to lighten the tone of the skin and remove blemishes and other discolorations. The active ascorbic acid in the said formulations can be that either covalently bound to carboxy-functional polysiloxanes, as well as free unconjugated ascorbic acid and mixtures thereof. Such formulations may optionally contain additional active compounds including vitamins, fragrances, anti-oxidants, herbal extracts, surfactants, humectants and the like.

One particular embodiment is directed to a keratinaceous tissue lightening agent comprising the inventive ester derivatives of either ascorbic acid or 2-keto acid-saccharides. In a specific embodiment the keratinaceous tissue comprises human skin. A further embodiment provides a composition comprising a safe and effective amount of the keratinaceous tissue lightening agent and a suitable vehicle or base. In a more specific embodiment the composition is in the form of an emulsion. In one aspect of these embodiments, the novel compound comprises the inventive ester derivatives of 2-keto-gulonic acid and is contemplated as a controlled release keratinaceous tissue lightening agent.

A further embodiment provides a method of lightening keratinaceous tissue comprising topical application of the compositions comprising the inventive ester derivatives of ascorbic acid. One particular embodiment provides a method of lightening keratinaceous tissue comprising topical application of a controlled release composition which comprises the inventive ester derivatives of either 2-keto-L-gulonic acid or 2-keto-D-gluconic acid. Such "controlled release," for example, may be achieved by delivery of a precursor which allows sustained release of ascorbic acid or undergoes subsequent conversion to free ascorbic acid. In a very specific embodiment the controlled release composition comprises inventive ester derivatives of 2-keto-L-gulonic acid.

Other embodiments are directed to personal care formulations comprising cosmetic or personal care compositions. Since the inventive ester derivatives exhibit a relatively-higher permeability to the skin and mucosa, they are desirable for cosmetic applications which generally include skin, hair, and orally-usable products. The inventive ester derivatives may also be mixed with other cosmetically suitable ingredients such as oily bases, water-soluble bases, flavors, colors, dyes, refrigerants, humectants, emollients, emulsifiers, gelation agents, viscosity enhancers, surfactants, stabilizers for foaming, clearances, antioxidants, germicides, putrefactive agents, coating-forming agents, and injection agents. The cosmetics according to the present invention contain at least 0.1 w/w %, and preferably at least 1.0 w/w % of the present inventive ester derivatives. It is also contemplated that the inventive ester derivatives may provide skin absorption enhancing effects to other benefit agents intended to provide benefit via absorption through the skin when administered in conjunction with those benefit agents.

The inventive ester derivatives may also be desirably mixed with one or more pharmaceutical or nutritive agents such as vitamins, amino acids, peptides, hormones, extracts, vasodilators, blood circulation-promoting agents, cell-activating agents, anti-inflammatory drugs, urtication-preventing agents, skin-function-promoting agents, enzymes, and keratolytics. The mixtures may be in the form of liquid, emulsion, cream, paste, powder, granule, or solid products. The personal care compositions according to the present invention contain at least 0.1 w/w %, and preferably at least 1.0 w/w % of the present inventive ester derivatives.

Also contemplated are formulations with minimal water content where an ascorbic acid siloxane ester is formulated with additional polysiloxane materials including polydimethylsiloxane, polydimethylsiloxane polyethers, siloxane resins and other organosiloxane compounds. Such formulations may also contain additional active compounds including vitamins, fragrances, anti-oxidants, herbal extracts and the like.

The following examples are offered as illustrations of particular embodiments of the present invention and should not be construed as limiting the scope thereof.

EXAMPLES

For purposes of the chemical analyses and summarized data discussed in the following examples, the following instrumentation information applies: 1) proton ($^1H$) nuclear magnetic resonance (NMR) spectra are recorded on a Varian Unity 300 NMR instrument operating at 300 MHz, all NMR spectra are referenced to tetramethylsilane (TMS) at 0 ppm and peak frequencies are recorded in ppm unless otherwise specified, samples are run in either deuterated chloroform ($CDCl_3$) or methanol ($CD_3OD$); 2) gas chromatography/mass spectrometry (GC/MS) is performed on an Agilent 6890 GC/MS with a split injector held at 200° C. and run at a split ratio of 20:1 interfaced into an HP-5MS capillary column (0.25 mm×30m×250 μm, Agilent, Calif.), injection volume is 1 μL and helium is the carrier gas, the flow rate is 1 mL/min and the oven program begins at 60° C. and increases to 320° C. at the rate of 25° C./min; and 3) electrospray mass spectrometry (ESI-MS) is performed on a TSQ Quantum triple quadrupole mass spectrometer (Thermo Finnegan, San Jose, Calif.) operating in positive mode.

Example 1

An enzymatic-catalyzed esterification reaction between L-Ascorbic acid and a mono-carboxydecyl functional polydimethylsiloxane is illustrated.

a.) Synthesis of 2,3,5,6-Tetra-O-trimethylsilyl-L-Ascorbic Acid

Ascorbic acid (13.6 g, 78 mmol) is added to a mixture of acetonitrile (ACN) (20 mL) and 1,1,1,3,3,3-hexamethyldisilazane (HMDZ) (35 ml, 333 mmol) with rapid (300 rpm) stirring. The mixture is stirred at room temperature in a vented flask until all solids completely dissolve (1-2 hours). The mixture is then diluted with toluene (100 mL) and concentrated under vacuum to give a straw-colored oil (35 g). Analysis of the liquid product indicates it to be predominantly 2,3,5,6-tetra-O-trimethylsilyl-L-ascorbic acid. $^1H$ NMR ($CDCl_3$, 300 MHz) δ 4.68 (s, H-4); 3.92 (ddd, H-5); 3.59, 3.68 (2 dd, H-6,6'), 0.02-0.5 (4s, 36H). GC/MS: m/z 465.2 [$M^+$].

b.) Enzyme-catalyzed Esterification

Tetra-TMS ascorbic acid (20 g, 43 mmol) and mono-(10-carboxydecyl)-functional polydimethylsiloxane (MCR-B11, Gelest, Pa.) (24 g, 22 mmol) are treated with N435 immobilized lipase (3.5 g) and t-amyl alcohol (10 mL) at 70° C. for 24 h under a blanket of nitrogen gas. Analysis of a small aliquot of the reaction mixture by $^1H$ NMR indicated greater than 90% conversion of the carboxylic acid groups to the 6-O-ascorbyl ester derivative. This is determined by the appearance of a new signal in the $^1H$ NMR spectrum, a triplet at 2.38 ppm attributable to the methylene group ($CH_2$) adjacent to esterified carboxylic functionalities. In addition, new signals are observed at 4.08 and 4.21 ppm and correspond to protons H-5, 6 and 6' of esterified ascorbic acid moieties. The reaction mixture is then filtered to remove the immobilized lipase and is treated with methanol (150 mL) at 50° C. for 2 h in order to remove the trimethylsilyl (TMS) ether groups masking the saccharide hydroxyl groups. The mixture is then concentrated under vacuum to give a viscous syrup (40 g). The syrup is then redissolved in methanol (150 mL) and added to deionized water (600 mL) with rapid stirring resulting in the formation of a white floc that is immediately collected by filtration on a Buchner funnel. The resulting solid is dried under high vacuum to give an off-white, waxy material that is shown to consist of a 1:1 mixture (molar basis) of ascorbic acid and the siloxane 6-O-ascorbyl ester (27 g) by $^1$H NMR. The siloxane ascorbic acid ester may be further purified by partition between 10% methanol in chloroform and water. Concentration of the organic phase under vacuum gives the siloxane 6-O-ascorbyl ester as a translucent wax with a soft consistency. $^1$H NMR (CD$_3$OD, 300 MHz) δ 4.72 (d, H-4); 4.21 (m, 2H, H-6,6'); 4.08 (ddd, H5); 2.38 (t, CH$_2$CO$_2$R); 1.60 (m, 2H); 1.20-1.45 (m, 14H); 0.92 (m, 2H); 0.58 (m, 2H); 0-0.2 (m, 60H).

Example 2

An enzyme-catalyzed esterification between L-Ascorbic acid (ASA) and a bis-carboxydecyl functional polydimethylsiloxane is illustrated.

Tetra-TMS ascorbic acid (synthesized according to part a), above, (23.8 g, 52 mmol) and bis-(10-carboxydecyl)-functional polydimethylsiloxane (DMS-B 12; Gelest, Pa.) (18.6 g, 18 mmol) in toluene (20 mL) are treated with immobilized lipase (N435, 5.2 g) at 70° C. for 48 hours. The mixture is then filtered to remove the immobilized lipase and treated with methanol (100 mL) for 12 h after which time the reaction mixture is concentrated to a tan colored syrup. Analysis of the material by $^1$H NMR reveals it to be a mixture of the mono- and bis-ascorbic acid esters of bis-(10-carboxydecyl)-functional polydimethylsiloxane, in addition to unchanged bis-(10-carboxydecyl)-functional polydimethylsiloxane. The syrup is partitioned between hexane and 90% aqueous methanol and the methanolic phase is concentrated under vacuum to give a mixture of the mono- and bis-ascorbic acid esters of bis-carboxydecyl functional polydimethylsiloxane as an off-white waxy solid (11 g). $^1$H NMR (CD$_3$OD, 300 MHz) δ 4.72 (d, H-4); 4.21 (m, H-6,6'); 4.08 (ddd, H5); 2.38 (t, CH$_2$CO$_2$H); 1.60 (m); 1.20-1.45 (m); 0.92 (m); 0.58 (m); 0-0.2 (m).

Example 3

An improved enzyme-catalyzed esterification between L-Ascorbic acid (ASA) and a bis-carboxydecyl functional polydimethylsiloxane is illustrated.

Tetra-TMS ascorbic acid (synthesized according to Example 1, part a), above, (50 g, 105 mmol) and bis-(10-carboxydecyl)-functional polydimethylsiloxane (Dow Corning, Mich.) (50 g, 35 mmol) in t-amyl alcohol (20 mL) are treated with immobilized lipase (N435, 10 g) at 70° C. for 28 hours under a blanket of nitrogen gas. The mixture is then filtered to remove the immobilized lipase and treated with methanol (100 mL) for 12 h after which time the reaction mixture is concentrated to a tan colored syrup. Analysis of the material by $^1$H NMR reveals that approximately 85% of the carboxylic functions are converted to 6-O-ascorbyl esters and that free ascorbic acid is also present in the product. The syrup is partitioned between 10% methanol in chloroform and water in order to remove the free ascorbic acid. Concentration of the organic phase under vacuum gives the carboxydecyl siloxane bis-(6-O-ascorbyl) ester as a friable wax (54 g). $^1$H NMR (CD$_3$OD, 300 MHz) δ 4.72 (d, H-4); 4.21 (m, H-6,6'); 4.08 (ddd, H5); 2.38 (t, CH$_2$CO$_2$R); 1.60 (m); 1.20-1.45 (m); 0.92 (m); 0.58 (m); 0-0.2 (m).

Example 4

An enzyme-catalyzed esterification between L-Ascorbic acid (ASA) and the methyl ester of a bis-carboxydecyl functional tetramethyldisiloxane is illustrated.

Tetra-TMS ascorbic acid (synthesized according to part a), above, (14.0 g, 30 mmol) and bis-1,3-(methyl 10-carboxydecyl)-1,1,3,3,-tetramethyldisiloxane (Dow Corning, Mich.) (5.3 g, 10 mmol) in t-Amyl alcohol (3 mL) are treated with immobilized lipase (N435, 2.6 g) at 70° C. for 48 hours under a blanket of dry nitrogen gas. The mixture is then treated with methanol (60 mL) for 12 h after which time the reaction mixture is concentrated to a tan colored syrup. Analysis of the material by $^1$H NMR reveals that approximately 70% of the carboxylic functions are converted to 6-O-ascorbyl esters resulting in a mixture of the mono- and bis-ascorbyl disiloxanes. $^1$H NMR (CD$_3$OD, 300 MHz) δ 4.71 (d, H-4); 4.20 (m, H-6,6'); 4.08 (ddd, H5); 2.38 (t, CH$_2$CO$_2$R); 2.30 (t, CH$_2$CO$_2$H), 1.62 (m); 1.20-1.45 (m); 0.54 (m); 0.15 (s). ESI-MS: m/z 836.24 [M+NH$_4$]$^+$ for bis-ASA ester of bis-(carboxydecyl)tetramethyldisiloxane; m/z 692.3 [M+NH$_4$]$^+$ for mono-ASA ester of bis-(carboxydecyl)tetramethyldisiloxane monomethyl ester.

Example 5

The following example illustrates chemical esterification between L-Ascorbic acid and a bis-carboxydecyl functional tetramethyldisiloxane using sulfuric acid as catalyst.

Ascorbic acid (11 g, 62.5 mmol) and bis-1,3-(10-carboxydecyl)-1,1,3,3-tetramethyldisiloxane (Gelest, Pa.) (5.02 g, 10.0 mmol) are dissolved in concentrated sulfuric acid (40 mL) at 4° C. and allowed to slowly warm to room temperature. The viscous, tan colored solution is stirred for 12 h after which it is added to 1000 mL of a 1:1 mixture of ice and water. The mixture is stirred until the ice melted and the white precipitate that forms is filtered and washed with water (250mL) followed by dissolution in methanol. The methanolic solution is adjusted to pH 3 by addition of sodium bicarbonate, filtered to remove salts and the solution concentrated to give a waxy solid. Analysis of this material by $^1$H NMR and mass spectrometry reveals it to be a 1:3 mixture of the 5-O- and 6-O-Ascorbyl esters of bis-1,3-(10-carboxydecyl)-1,1,3,3-tetramethyldisiloxane. $^1$H NMR (CD$_3$OD, 300 MHz) δ 5.24 (dt, H-5); 4.72 (d, H-4); 4.20 (m, H-6,6'); 4.08 (m, H-5); 3.75 (m, H-6,6'); 2.38 (t, CH$_2$CO$_2$R); 2.28 (t, CH$_2$CO$_2$H), 1.5-1.7 (m); 1.20-1.45 (m); 0.45-0.60 (m); 0.05 (s, SiMe$_2$). ESI-MS: m/z 836.06 [M+NH$_4$]$^+$ for bis-ASA ester of bis-(carboxydecyl)tetramethyldisiloxane.

Example 6

The following example illustrates chemical esterification between L-Ascorbic acid and bis-carboxypropyl-functional polydimethylsiloxane.

2,3,5,6-Tetra-O-trimethylsilyl-L-Ascorbic acid is treated with cold methanol to selectively remove the 6-O-TMS ether, followed by removal of the solvent under vacuum. The resulting crystalline 2,3,5-tri-O-trimethylsilyl-L-Ascorbic acid (400 mg, ~1 mmol) is treated with bis-(3-carboxypropyl)- functional polydimethylsiloxane (500 mg, ~0.5 mmol) in the presence of dicyclohexylcarbodiimide (DCC) (1.5 mL of a 1M solution in dichloromethane, 1.5 mmol) and dimethylaminopyridine (DMAP) (30 mg, 0.25 mmol). A white precipitate is observed to form after a few minutes. After a period of additional stirring (1 h), the mixture is filtered to remove the precipitate and concentrated under vacuum to give an oil. Analysis of this oil by $^1$H NMR reveals the appearance of signals indicative of partial esterification of ascorbic acid, namely signals in the 4.0 to 4.3 ppm region of the $^1$H NMR spectrum.

Example 7

An enzyme-catalyzed synthesis of a 2-Keto-L-gulonic (KLG) acid functional disiloxane is illustrated.

2,3:4,5-diisopropylidene-2-keto-L-gulonic acid (dikegulac) (5.8 g, 20 mmol) and 1,3-bis-(3-hydroxypropyl)-1,1,3,3-tetramethyldisiloxane (2.5 g, 10 mmol) are dissolved in tetrahydrofuran (THF)(25 mL) containing 3 A molecular sieves (0.3 g) and treated with N435 immobilized enzyme (0.8 g) at reflux for 5 days. The reaction is filtered to remove the immobilized enzyme and molecular sieves and then concentrated under vacuum to give a pale yellow viscous oil mixed with white crystals. The mixture is extracted with cold hexane (50 mL) and the hexane extract is concentrated to give a mixture of mono- and diacylated product (1.9 g). ESI-MS: m/z 529 [M+Na]$^+$ (mono-acylated product). M/z 785.2 [M+Na]$^+$ (di-acylated product).

Example 8

Chemical synthesis of a 2-KLG functional disiloxane is illustrated.

2,3:4,5-diisopropylidene-2-keto-L-gulonic acid (2.92 g, 10 mmol) and 1,3-bis-(3-hydroxypropyl)-1,1,3,3-tetramethyldisiloxane (1.3 g, 5 mmol) are dissolved in dichloromethane (DCM) (50 mL) to which is added dimethylaminopyridine (DMAP) (92 mg) and dicyclohexycarbodiimide (8 mL of 1 M in DCM) with stirring at room temperature (23° C.). A white precipitate is observed to form. After 2 additional hours the reaction mixture is filtered and concentrated under vacuum to give a partially crystalline solid. This material is applied to a column of silica gel (40 g) and eluted with ethyl acetate/hexane (1:2) to give the mono-2-KLG-functional disiloxane as a viscous oil (0.8 g). $^1$H NMR (CDCl$_3$, 300 MHz) δ 4.26 (d, 1H); 4.18 (t, 2H); 4.02-4.14 (m, 3H); 3.54 (m, 2H); 1.50-1.75 (m, 4H); 1.30, 1.38, 1.48 (3s, 12H); 0.50 (m, 4H); 0.1 (m, 12H).

Example 9

A composition comprising a skin-lightening agent and sunscreen is illustrated. The illustrative composition is in the form of a cream.

TABLE 1

| Ingredient (INCI name) | Wt. % | Trade Name/Supplier |
|---|---|---|
| PHASE A | | |
| 1. Ascorbyl Undecyl Dimethiconate | 3.60 | |
| 2. Caprylic/Capric Triglyceride | 6.40 | Liponate CG |
| 3. Ethylhexyl Methoxycinnamate | 7.00 | Escalol 557/ International Specialty Products |
| 4. Polyacrylamide and C13-14 Isoparaffin and Laureth-7 | 3.00 | Sepigel 305/SEPPIC. |

TABLE 1-continued

| Ingredient (INCI name) | Wt. % | Trade Name/Supplier |
|---|---|---|
| PHASE B | | |
| 5. Glycerin | 4.00 | |
| 6. Deionized Water | 75.75 | |
| 7. Diazolidinyl Urea and Iodopropynyl Carbamate | 0.25 | Liquid Germall Plus/ Sutton Laboratories |

PROCEDURE: Combine ingredients 1 and 2 in a small mixing vessel. Warm to approximately 50° C. and mix to disperse ingredient 1 into ingredient 2. After a homogenous mixture is obtained, allow to cool and add ingredients 3 and 4. Mix until homogenous. In another mixing vessel that is large enough to hold the entire batch combine the ingredients for Phase B (5-7) and mix until homogenous. Slowly add Phase A (ingredients 1-4) to Phase B while mixing vigorously to ensure that Phase A is rapidly incorporated into the batch. The mixer speed should be increased as the viscosity of the formulation increases to ensure proper mixing. After all of Phase A has been added, mix for 10-15 minutes, scraping the sides of the mixing vessel occasionally, if necessary.

Example 10

A composition comprising a skin-lightening agent is illustrated. The illustrative composition is in the form of a cream.

TABLE 2

| Ingredient (INCI name) | Wt. % | Trade Name/Supplier |
|---|---|---|
| PHASE A | | |
| 1. Ascorbyl Undecyl Dimethiconate | 3.60 | |
| 2. Cyclopentasiloxane | 6.40 | Dow Corning 245 Fluid/Dow Corning |
| 2. Sunflower Oil | 8.00 | |
| 4. Sodium Polyacrylate and Mineral Oil and Trideceth-6 | 2.00 | Flocare ET 75/SNF |
| PHASE B | | |
| 5. Glycerin | 4.00 | |
| 6. Deionized Water | 75.75 | |
| 7. Diazolidinyl Urea and Iodopropynyl Carbamate | 0.25 | Liquid Germall Plus/Sutton Laboratories. |

PROCEDURE: Combine ingredients 1 and 2 in a small mixing vessel. Warm to approximately 50° C. and mix to disperse ingredient 1 into ingredient 2. After a homogenous mixture is obtained, allow to cool and add ingredients 3 and 4. Mix until homogenous. In another mixing vessel that is large enough to hold the entire batch combine the ingredients for Phase B (5-7) and mix until homogenous. Slowly add Phase A (ingredients 1-4) to Phase B while mixing vigorously to ensure that Phase A is rapidly incorporated into the batch. The mixer speed should be increased as the viscosity of the formulation increases to ensure proper mixing. After all of Phase A has been added, mix for 10-15 minutes, scraping the sides of the mixing vessel occasionally, if necessary.

Example 11

A composition comprising a skin-lightening agent is illustrated. The illustrative composition is in the form of a lotion.

TABLE 3

| Ingredient (INCI name) | Wt. % | Trade Name/Supplier |
|---|---|---|
| PHASE A | | |
| 1. Ascorbyl Undecyl Dimethiconate | 7.00 | |
| 2. Cyclopentasiloxane | 12.30 | Dow Corning 245 Fluid/Dow Corning |
| PHASE B | | |
| 3. Acrylates/C10-30 Alkyl Acrylate Crosspolymer | 0.12 | Pemulen TR2/Noveon |
| 4. Triethanolamine | 0.10 | |
| 5. DM DM Hydantoin | 0.30 | Glydant/Lonza |
| 6. Water | 80.18 | |

PREPARATION: Combine the ingredients for Phase A (1-2) in a small beaker or other suitable mixing vessel. Warm to approximately 50° C. and mix to disperse ingredient 1 into ingredient 2. In a second mixing vessel that is large enough to contain the entire batch, disperse ingredient 3 into ingredient 6. Ingredient 3 should be added slowly to prevent clumping and the mixing should be vigorous enough to rapidly disperse it into the water but not so vigorous as to generate foam. After all of ingredient 3 has been added, mix for 5-10 minutes to ensure that it is well-dispersed. Add ingredients 4 and 5 mix until homogenous and then heat Phase B to approximately 50° C. Slowly add Phase A to Phase B while mixing with sufficient agitation to ensure that Phase A is rapidly incorporated into the batch. Continue mixing and allow the batch to cool to room temperature.

Example 12

This example illustrates cell viability properties and efficacy of skin lightening formulations according to the present invention. For purposes of these examples, DP2 and DP15 both refer to a bis-ascorbyl ester of a (10-carboxydecyl)-terminated dimethylsiloxane, but with the former having two degrees of polymerization, and the latter having an average of 15 degrees of polymerization (15+/−5). In particular, three formulations according to the present invention, water (a negative control), 1% kojic acid (Sigma, Wis.) in water (positive control), and 2.3% ascorbyl palmitate in DMI (dimethyl isosorbide from Uniqema Americas, representative of a currently commercially available skin-lightening compound), were assayed and compared for cell viability and skin lightening efficacy (see Table 4). The assays were carried out using Melanoderm tissue model MEL 300 A cell line (Melano-Derm™ tissue model available from MatTek, Ashland, Mass.). This melanoderm model consists of normal, human-derived epidermal keratinocytes and melanocytes that have been co-cultured to form a multilayer, highly differentiated model of human epidermis.

TABLE 4

Formulations Assayed

| Compound | Carrier | Concentration | Dosed |
|---|---|---|---|
| Ascorbyl Palmitate | DMI | 2.3% | 10 µL |
| DP2 | DMI | 2.3% | 10 µL |
| DP15 | DMI | 5.48% | 10 µL |
| DP2 with extra ascorbic acid | DMI | 1.5% | 10 µL |

Negative control: 25 µL water
Positive control: 25 µL kojic acid (a) Viability Assay Duplicate samples of each of the formulations in Table 4 were dosed and tested for 48 hours for cell viability by MTT assay (MatTek MTT ET-50 protocol). The volume of water and kojic acid used was 25 ul. The volume of test article used was 10 ul based on results from a previous experiment that revealed cytotoxicity at 25 ul. Viability results using the MTT assay are presented in Table 5.

TABLE 5

Viability by MTT

| | Water | 10 uL Asc. Palmitate | 10 uL DP2/DMI |
|---|---|---|---|
| | 1.585 | 1.569 | 1.433 |
| | 1.521 | 1.507 | 1.401 |
| Average | 1.553 | 1.538 | 1.417 |
| % Viability | | 99.03 | 91.24 |
| | 1.486 | 1.364 | 1.603 |
| | 1.445 | 1.358 | 1.619 |
| Average | 1.4655 | 1.361 | 1.611 |
| % Viability | | 92.87 | 109.93 |
| Total average) | 1.50925 | 1.4495 | 1.514 |
| % Viability | | 96.04 | 100.31 |
| Standard Dev. | | 4.36 | 13.21 |

MTT viability data shows that cell viability with DP2 in DMI is >90% and that a 10 uL dose does not cause cytotoxicity, confirming results of a previous study, which suggested that cytotoxicity at the 25 uL dose is probably caused by the carrier, DMI.

b) Melanin Content

Figure 4A:
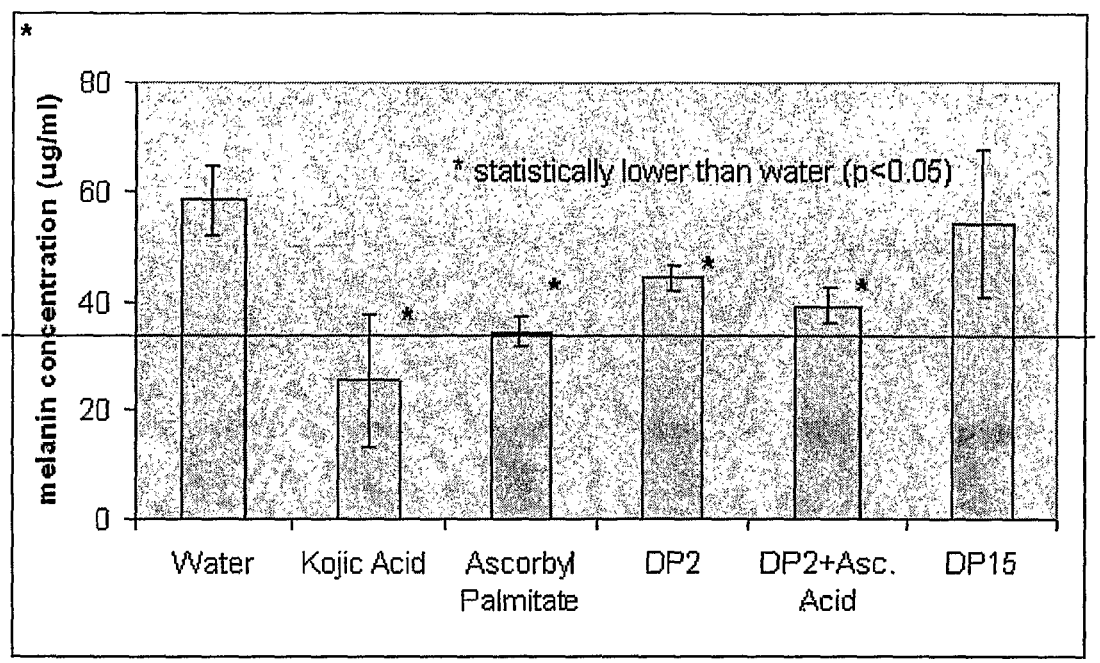
FIG. 4 (a) illustrates Melanin concentrations (ug/ml) after day 10 of the cell viability and (b) illustrates skin lightening assay according to the Mat Tek MTT ET-50 test protocol.
Figure 4B:
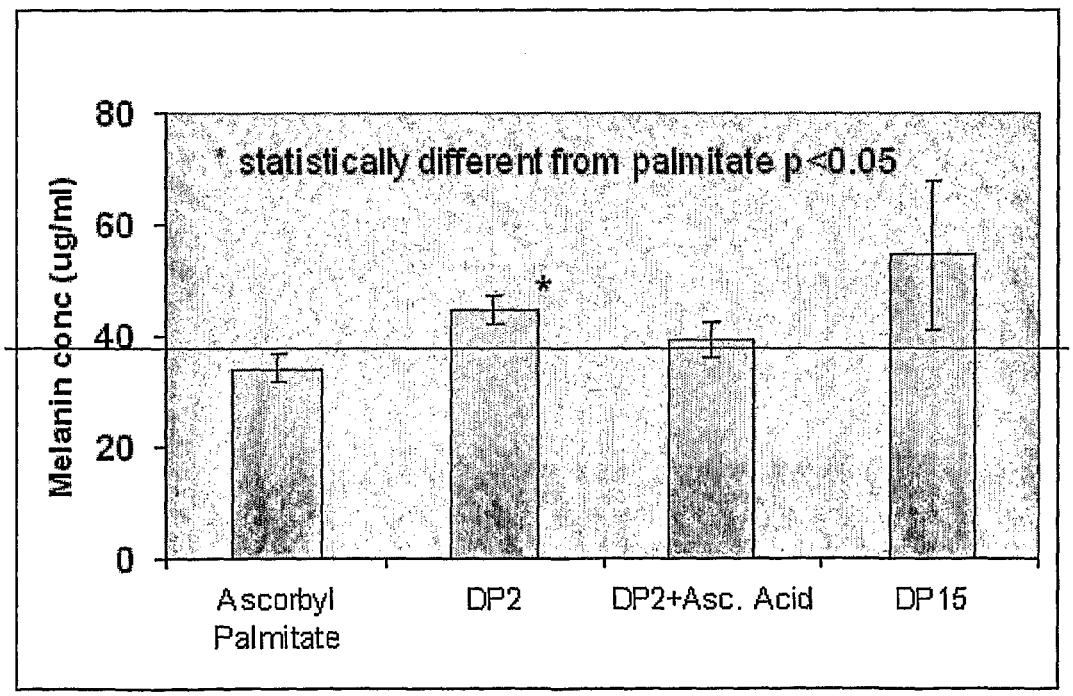

Table 6 (see FIG. 4(a)) sets forth the melanocyte concentration (ul/ml) after 6 applications of each formulation as indicated. Melanin concentration (ug/ml) was lower (p<0.05) in the positive control (kojic acid) and in Ascorbyl palmitate, DP2, and DP2+ascorbic acid. Table 7 (see FIG. 4(b)) also sets forth the melanocyte concentration on Day 10, after six applications of the test formulations. Melanin concentration (ug/ml) was higher (p<0.05) in DP2, with no difference from DP2+ascorbic acid or DPI 5. However, p value for DP15 had high variability and statistical difference was borderline (p=0.06)

TABLE 6

Melanin Concentration at Day 10
Test Preparations vs. Water

| | Water | Kojic Acid | Ascorbyl Palmitate | DP2 | DP2 + Asc. Acid | DP15 |
|---|---|---|---|---|---|---|
| Avg. | 58.61 | 25.20 | 34.14 | 44.40 | 39.27 | 54.36 |
| SD | 6.36 | 12.29 | 2.65 | 2.45 | 3.36 | 13.42 |
| p value | | 0.014 | 0.004 | 0.023 | 0.010 | 0.646 |

TABLE 7

Melanin Concentration at Day 10
Test Preparations vs. Palmitate

|  | Ascorbyl Palmitate | DP2 | DP2 + Asc. Acid | DP15 |
|---|---|---|---|---|
| Avg | 34.14 | 44.40 | 39.27 | 54.36 |
| SD | 2.65 | 2.45 | 3.36 | 13.42 |
| p value |  | 0.008 | 0.106 | 0.063 |

Example 13

This example illustrates that compounds according to the present invention are surprisingly easy to formulate compared to conventionally employed compounds such as ascorbyl palmitate. The presently inventive compounds are less viscous, softer, and exhibit improved dispersibility over ascorbyl palmitate.

a) Approximately 7.2 g of a sample of a material of the present invention comprising an undecyl ascorbate group on one end of the short chain dimethylsiloxane (Formula=$Si(CH_3)_3$-[$Si(CH_3)_2$]$_8$—[$CH_2$]$_{10}$—COO-Ascorbate), with a calculated molecular weight of 1082) was weighed into a glass vial. Liponate CG (INCI name: caprylic/capric triglyceride) was added to the vial to bring the net weight to 20 g. The vial was warmed in a water bath set at 50° C. The material easily dispersed into the Liponate CG and formed a translucent gel upon cooling. A sample of ascorbyl palmitate obtained from DSM was also tested for dispersibility in Liponate CG. Several concentrations were tested. The lowest concentration tested was made by weighing approximately 2.3 g of ascorbyl palmitate into a glass vial and then adding caprylic/capric triglyceride to bring the net weight to 20 g. Even at this lower concentration, the ascorbyl palmitate would not disperse in the caprylic/capric triglyceride after heating in a water bath at temperatures ranging from 50° C. to 90° C. for 20-30 minutes.

b) Approximately 7.2 g of an undecyl ascorbate, described in part (a), was weighed into a glass vial with a low molecular-weight silicone fluid, Dow Corning® 245 Fluid (INCI name: cyclopentasiloxane). The silicone was added to the vial to bring the net weight to 20 g. After warming in a water bath set at 50° C., the material easily dispersed into the cyclopentasiloxane to form a translucent mixture. This mixture thickened upon cooling to room temperature. To determine if the mixture was a stable dispersion or an unstable suspension, the mixture was centrifuged in a bench top laboratory centrifuge at 3000 rpm for approximately 30 minutes. After centrifuging, the sample had a small layer of white material on the bottom of the vial. The amount of white material was small (much less than the amount of siloxane undecyl ascorbate that was used) and it was later determined that the white material was most likely unreacted ascorbic acid. A sample of ascorbyl palmitate obtained from DSM was tested for dispersibility in Dow Corning® 245 Fluid. Several concentrations were tested. The lowest concentration tested was made by weighing approximately 2.3 g of ascorbyl palmitate into a glass vial and then adding Dow Corning® 245 Fluid to bring the net weight to 20 g. Even at this lower concentration, the ascorbyl palmitate would not disperse in the Dow Corning® 245 Fluid after heating in a water bath at temperatures ranging from 50° C. to 90° C. for 20-30 minutes.

c) Approximately 0.35 g of a sample of a material according to the present invention comprising an undecyl ascorbate group on both ends of a disiloxane (Formula=Ascorbyl-OCO[$CH_2$]$_{10}$—$Si(CH_3)_2OSi(CH_3)_2$—[$CH_2$]$_{10}$—COO-Ascorbate) was weighed into a glass vial. Deionized water was added to bring the total net weight to 3.5 g. The vial was placed in a water bath set at 60° C. and the disiloxane material began to disperse after a few minutes. The vial was pulled out of the water bath periodically over the next 10-15 minutes. A thick hazy dispersion was formed. Upon cooling the vial was examined to determine if all of the test material had been dispersed. It was difficult to tell due to the hazy appearance of the sample. The experiment was repeated with approximately 0.17 of the disiloxane diluted to 3.5 g with deionized water. This mixture produced a thinner, less hazy dispersion after warming in the water batch. Both dispersions were stable for several weeks, with no sign of separation or settling of the test material. Ascorbyl palmitate obtained from DSM was tested for dispersibility in deionized water. It was not dispersible at concentrations comparable to those tested for the disiloxane test material.

The invention claimed is:

1. A compound comprising an ester derivative of ascorbic acid or 2-keto acid saccharide, wherein an ester has been introduced by an ester bond formation between an ascorbic acid or a 2-keto acid saccharide comprising at least one hydroxy-functional group and a carboxy-functional organosiloxane, wherein the ascorbic acid comprises either ascorbic acid or isoascorbic acid, or stereoisomers or salts thereof, and wherein the 2-keto acid saccharide comprises either 2-keto-L-gulonic acid or 2-keto-D-gluconic acid, or stereoisomers or salts thereof.

2. The compound as recited in claim 1, wherein the organosiloxane comprises mono or bis-carboxy-functional organosiloxane, or a combination thereof.

3. The compound as recited in claim 1, wherein the organosiloxane comprises pendant carboxy-functional organosiloxane.

4. The compound as recited in claim 1, wherein the ester derivative comprises a 6-O acyl derivative of ascorbic acid.

5. The compound as recited in claim 1, wherein the ester derivative comprises a 6-O acyl derivative of a methyl 2-keto acid saccharide.

6. The compound as recited in claim 1, wherein the ascorbic acid comprises at least one hydroxy group which is functionalized or protected or both.

7. The compound as recited in claim 6, wherein the at least one hydroxy group is protected by formation of an ester, an ether, or an epoxy.

8. The compound as recited in claim 7, wherein the ester is selected from the group consisting of an O-acetate, an O-carbonate, and an O-phosphate.

9. The compound as recited in claim 7, wherein the ether comprises a trimethylsilyl ether.

10. A compound as recited in claim 1, wherein the compound comprises an ester derivative of ascorbic acid having the following structural formula:

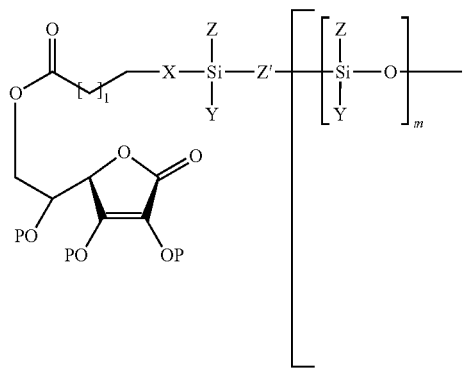

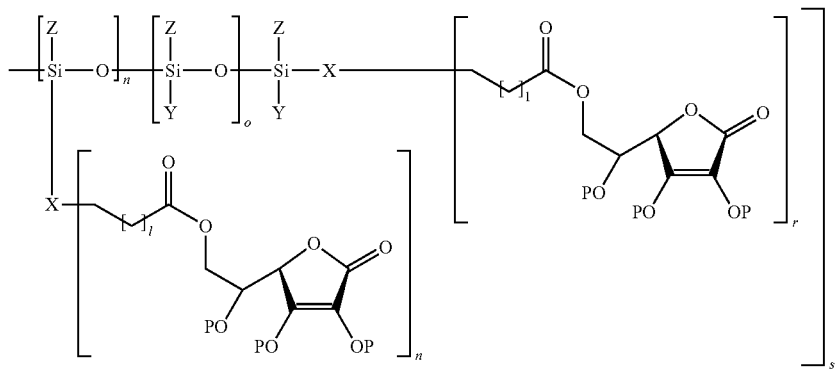

and wherein: each P may independently be any protecting or functional group, a proton or a cation chosen from the alkali or alkaline earth metals; the stereochemical configurations of the fourth and/or fifth carbons of the ascorbic acid moieties are independently selected; s is either 0 or 1; m, n, and o may independently represent any integer between 0 and 300; l is any integer between 0 and 30; r is either 0 or 1; X may be $CH_2$, $CH_3$, $OCH_2[CH_2]_l CH_2$, $OCH_2CH(CH_3)CH_2$, $(OCH_2CH_2)_m OCH_2[CH_2]_l CH_2$, $(OCH(CH_3)CH_2)_m OCH_2[CH_2]_l CH_2$, $NHCH_2[CH_2]_l CH_2$, $NHCH_2CH_2NHCH_2[CH_2]_l CH_2$, $NHCH_2CH_2NHCH_2CH(CH_3)CH_2$, $(C=O)NHCH_2[CH_2]_l CH_2$, $(C=O)NHCH_2CH_2NHCH_2[CH_2]_l CH_2$, or $(C=O)NHCH_2CH_2NHCH_2CH(CH_3)CH_2$, and X may also be Y or Z; Y and Z are independently selected from H, OH, alkyl $(C_{1-12})$, carboxyalkyl $(C_{1-12})$, alkenyl $(C_{1-12})$, $OSi(CH_3)_3$, $[OSi(Y)(Z)]_m OSi(X)(Y)(Z)$, and phenyl; and further wherein when s=1, Z'=O, and when s=0, Z'=Z.

11. A compound as recited in claim 1, wherein the compound comprises an ester derivative of a 2-keto acid saccharide having the following structural formula:

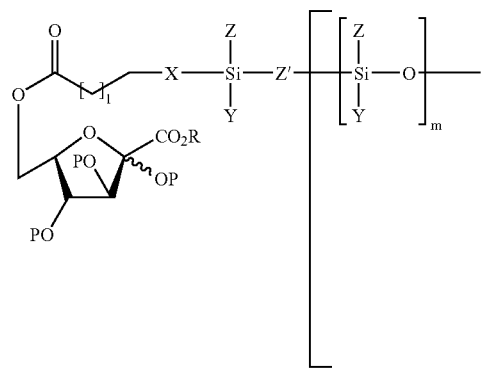

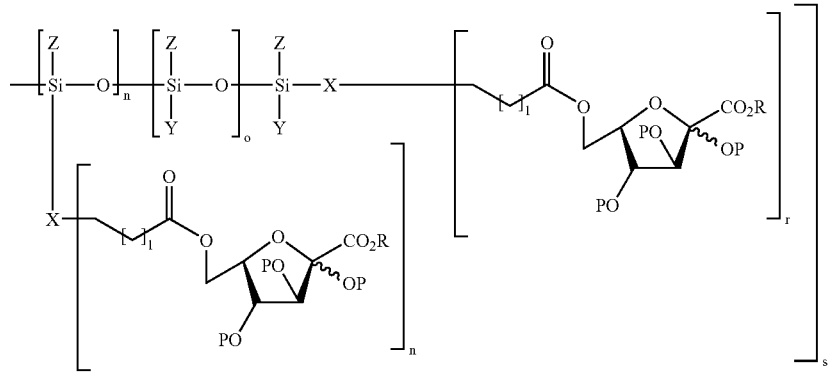

and wherein: each P is independently be any protecting or functional group, a proton or a cation chosen from the alkali or alkaline earth metals; R is a lower alkyl (C1-6) or alkenyl (C1-6), a metal ion, $NH_4^+$ or $NH_a(R)_{4-a}$; where R is lower alkyl (C1-6) and a is an integer from 0 to 4, the stereochemical configurations of the fourth and/or fifth carbons of the carbohydrate moieties are independently selected; s is either 0 or 1; m, n, and o may independently represent any integer between 0 and 300; l is any integer between 0 and 30; r is either 0 or 1; X may be $CH_2$, $CH_3$, $OCH_2[CH_2]_lCH_2$, $OCH_2CH(CH_3)CH_2$, $(OCH_2CH_2)_mOCH_2$-$[CH_2]_lCH_2$, $(OCH(CH_3)CH_2)_mOCH_2[CH_2]_lCH_2$, $NHCH_2[CH_2]_lCH_2$, $NHCH_2CH_2NHCH_2[CH_2]_lCH_2$, $NHCH_2CH_2NHCH_2CH(CH_3)CH_2$, $(C=O)$ $NHCH_2[CH_2]_lCH_2$, $(C=O)NHCH_2CH_2NHCH_2[CH_2]_lCH_2$, or $(C=O)NHCH_2CH_2NHCH_2CH(CH_3)CH_2$, and X may also be Y or Z; Y and Z are independently selected from H, OH, alkyl (C1-12), carboxyalkyl (C1-12), alkenyl (C1-12), $OSi(CH_3)_3$, $[OSi(Y)(Z)]_mOSi(X)(Y)(Z)$, and phenyl; and further wherein when s=1, Z'=O, and when s=0, Z'=Z.

12. A compound comprising an ester derivative of a 2-keto-acid saccharide, wherein an ester has been introduced by an ester bond formation between a 2-keto-gulonic acid and a carbinol-functional organosiloxane, and wherein the 2-keto acid saccharide comprises either 2-keto-L-gulonic acid or 2-keto-D-gluconic acid, or stereoisomers or salts thereof.

13. The compound as recited in claim 12 wherein the organosiloxane comprises a mono or bis-carbinol functional organosiloxane, or a combination thereof.

14. The compound as recited in claim 12, wherein the 2-keto acid saccharide comprises at least one hydroxy group which is functionalized or protected or both.

15. The compound as recited in claim 14, wherein the at least one hydroxy group is protected by formation of an ester, an ether, or an epoxy.

16. The compound as recited in claim 15, wherein the ester is selected from the group consisting of an O-acetate, an O-carbonate, and an O-phosphate.

17. The compound as recited in claim 15, wherein the ether comprises an isopropylidene ether.

18. A compound as recited in claim 12 having the following structural formula:

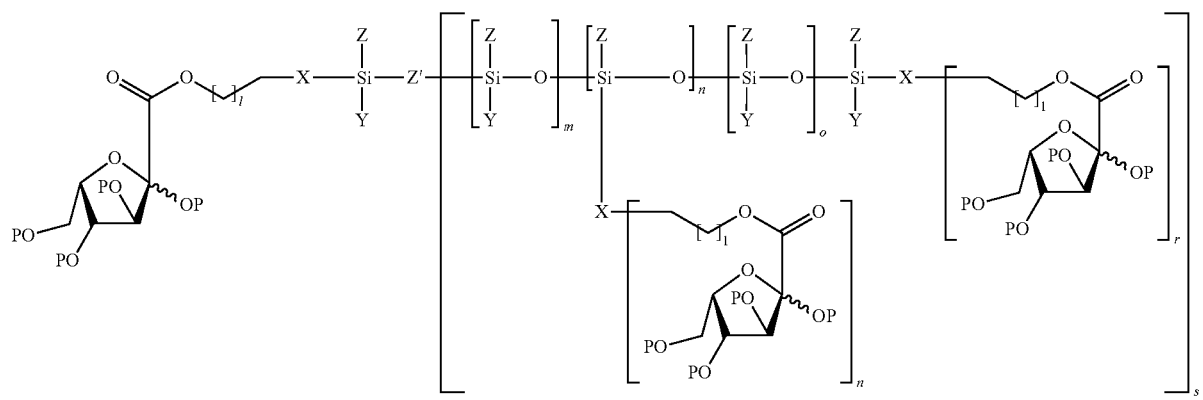

and wherein P may be any protecting or functional group or a proton, R may be a lower alkyl (C1-6) or alkenyl (C1-6), a metal ion, $NH_4^+$, or $NH_s(R)_{4-s}$ where R is lower alkyl (C1-6) and s is either 0 or 1, s is an integer from 0 to 4, the stereochemical configurations of the fourth and/or fifth carbons of the carbohydrate moieties are independently selected; m, n, o and p may be independently represented by any integer between 0 and 300, and l may be any integer between 1 and 30, X may be independently selected from the group consisting of $CH_2$, $CH_3$, $OCH_2[CH_2]_lCH_2$, $OCH_2CH(CH_3)CH_2$, $(OCH_2CH_2)_mOCH_2[CH_2]_lCH_2$, $(OCH(CH_3)CH_2)_mOCH_2[CH_2]_lCH_2$, $NHCH_2[CH_2]_lCH_2$, $NHCH_2CH_2NHCH_2[CH_2]_lCH_2$, $NHCH_2CH_2NHCH_2CH(CH_3)CH_2$, $(C=O)NHCH_2[CH_2]_lCH_2$, $(C=O)NHCH_2CH_2NHCH_2[CH_2]_lCH_2$, $(C=O)NHCH_2CH_2NHCH_2CH(CH_3)CH_2$, Y or Z, and Y and Z are independently selected from H, OH, alkyl (C1-12), alkenyl (C1-12), OSi(CH$_3$)$_3$, [OSi(Y)(Z)]$_m$OSi(X)(Y)(Z), and phenyl; and further wherein when s=1, Z'=O, and when s=0, Z'=Z.

19. A method for synthesizing the compound recited in claim 1 comprising:
   a) providing a protected ascorbic acid or a protected 2-keto acid saccharide by forming a protecting group from at least one hydroxy-functional group thereon;
   b) mixing the protected ascorbic acid or protected 2-keto acid saccharide with a carboxy-functional siloxane to form a solution;
   c) contacting the solution with a biocatalyst which is capable of catalyzing ester bond formation;
   d) optionally, removing the protecting group, and
   wherein the protecting group may comprise a functional group.

20. The method as recited in claim 19, wherein the protecting group comprises a trimethylsilyl ether.

21. The method as recited in claim 19, wherein the carboxy-functional organosiloxane is mono- or bis-carboxy functional.

22. The method as recited in claim 19, wherein the biocatalyst comprises an enzyme.

23. The method as recited in claim 22, wherein the enzyme comprises a hydrolase enzyme.

24. The method as recited in claim 23, wherein the hydrolase enzyme exits in either free or immobilized form and is selected from the group consisting of a lipase, a protease, a phosphoesterase, an esterase, a cutinase, and combinations thereof.

25. The method as recited in claim 24, wherein the hydrolase enzyme comprises a lipase.

26. The method as recited in claim 25, wherein the lipase comprises an immobilized form of *Candida antarctica* lipase B.

27. A method for synthesizing the compound recited in claim 12 comprising:
   a) providing a protected 2-keto acid saccharide by forming a protecting group from at least one of the hydroxy-functional groups;
   b) providing a mono or bis-carbinol-functional organosiloxane;
   c) dissolving the protected 2-keto acid saccharide and the carbinol-functional organosiloxane in a suitable solvent to form a solution;
   d) treating the solution with a biocatalyst which is capable of catalyzing ester bond formation;
   e) optionally, removing the protecting group, and
   wherein the protecting group may comprise a functional group.

28. The method as recited in claim 27, wherein the protecting group comprises an alkylidene.

29. The method as recited in claim 28, wherein the alkylidene comprises acetonide.

30. The method as recited in claim 27, wherein the biocatalyst comprises an enzyme.

31. The method as recited in claim 30, wherein the enzyme comprises a hydrolase enzyme.

32. The method as recited in claim 31, wherein the hydrolase enzyme is selected from the group consisting of a lipase, a protease, a phosphoesterase, an esterase, a cutinase, and combinations thereof.

33. The method as recited in claim 32, wherein the hydrolase enzyme comprises a lipase.

34. The method as recited in claim 33, wherein the lipase comprises an immobilized form of *Candida antarctica* lipase B.

35. A controlled-release method of generating ascorbic acid comprising:
   a) providing an ester derivative of 2-keto L-gulonic acid wherein the ester has been introduced by an ester bond formation between a 2-keto L-gulonic acid and a carbinol-functional organosiloxane;
   b) delivering the acyl deriviative of 2-keto L-gulonic acid to an environment wherein an intramolecular lactonization reaction may occur, releasing free ascorbic acid and a carbinol-functional organosiloxane.

36. A composition comprising the compound as recited in claim 1.

37. A composition according to claim 36, further comprising free ascorbic acid.

38. A treatment or cosmetic formulation comprising: an ester derivative of 2-keto L-gulonic acid wherein the ester has been introduced by an ester bond formation between a 2-keto L-gulonic acid and a carbinol-functional organosiloxane; and a pharmaceutically or cosmetically suitable vehicle or base.

39. A keratinaceous tissue lightening agent comprising the compound recited in claim 1.

40. The agent as recited in claim 39, wherein the keratinaceous tissue comprises human skin.

41. A composition comprising: a safe and effective amount of the keratinaceous tissue lightening agent recited in claim 39; and a suitable vehicle or base.

42. The composition as recited in claim 41, further comprising free ascorbic acid.

43. The composition as recited in claim 41, wherein the compound has a degree of polymerization (DP) based on the values of s, m, n and o, further wherein s, m, n and o are varied so that the degree of polymerization ranges from 1 to about 300.

44. The composition as recited in claim 43, wherein s, m, n and o are varied so that the degree of polymerization ranges from 1 to about 100.

45. The composition as recited in claim 44, wherein s, m, n and o are varied so that the degree of polymerization ranges from 2 to about 20.

46. The composition as recited in claim 43, wherein the compound comprises a bis-ascorbyl ester of a (10-carboxy-decyl)-terminated polydimethylsiloxane, wherein l=9, X=CH$_2$, Y=Z=CH$_3$, Z'=O, s=1, n=0, and o=0, further wherein m=2, or m=13, on average.

47. The composition as recited in claim 41, wherein the composition is in the form of an emulsion.

48. A method of lightening keratinaceous tissue comprising: topically applying the composition as recited in claim 41 to human skin.

49. A personal care composition comprising an ester derivative of ascorbic acid, wherein an ester has been introduced by an ester bond formation between an ascorbic acid comprising at least one hydroxy-functional group and a carboxy-functional organosiloxane, wherein the ascorbic acid comprises either ascorbic acid or isoascorbic acid, or stereoisomers or salts thereof.

50. A personal care composition comprising the compound as recited in claim 6 wherein the functionalized hydroxy group imparts an additional beneficial property.

* * * * *